US010438576B2

(12) United States Patent
Todd et al.

(10) Patent No.: US 10,438,576 B2
(45) Date of Patent: Oct. 8, 2019

(54) ACTIVE NOISE CANCELLATION IN AN OPHTHALMIC SURGICAL SYSTEM

(71) Applicant: Novartis AG, Basel (CH)

(72) Inventors: Kirk Wellington Todd, Yorba Linda, CA (US); Johan Gustaf Ekvall, Laguna Beach, CA (US); Paul J. Essex, Rancho Santa Margarita, CA (US); Steven T. Charles, Memphis, TN (US); Nicholas Max Gunn, Newport Beach, CA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 15/646,759

(22) Filed: Jul. 11, 2017

(65) Prior Publication Data

US 2018/0018953 A1    Jan. 18, 2018

Related U.S. Application Data

(60) Provisional application No. 62/361,217, filed on Jul. 12, 2016.

(51) Int. Cl.
*G10K 11/178*    (2006.01)
*A61F 9/007*    (2006.01)
*A61B 17/00*    (2006.01)

(52) U.S. Cl.
CPC ........ *G10K 11/178* (2013.01); *A61F 9/00763* (2013.01); *G10K 11/17875* (2018.01); *A61B 2017/00544* (2013.01); *A61B 2217/007* (2013.01); *G10K 2210/109* (2013.01); *G10K 2210/116* (2013.01); *G10K 2210/3026* (2013.01)

(58) Field of Classification Search
CPC ........... G10K 11/178; G10K 2210/109; G10K 2210/3026; G10K 11/17875; G10K 2210/116; A61F 9/00763; A61B 2017/00544; A61B 2217/007
USPC ......................................................... 381/71.3
See application file for complete search history.

(56) References Cited

U.S. PATENT DOCUMENTS

| 4,677,676 A | 6/1987 | Eriksson |
| 4,677,677 A | 6/1987 | Eriksson |
| 9,918,669 B2 * | 3/2018 | Brown ................. A61B 5/0024 |

\* cited by examiner

*Primary Examiner* — Paul Kim

(57) ABSTRACT

Active noise cancellation is employed to address unwanted acoustical noise generated by various equipment associated with an ophthalmic surgical system. Active noise cancellation may be used within a chassis of the ophthalmic surgical system, within an air compressor used with the ophthalmic surgical system, and within a reciprocating surgical probe used with the ophthalmic surgical system.

10 Claims, 4 Drawing Sheets

ACTIVE NOISE CANCELLATION IN AN OPHTHALMIC SURGICAL SYSTEM

BACKGROUND

Field of the Disclosure

The present disclosure relates to ophthalmic surgery, and more specifically, to active noise cancellation in an ophthalmic surgical system.

Description of the Related Art

In ophthalmology, eye surgery, or ophthalmic surgery, is performed on the eye and accessory visual structures. More specifically, vitreoretinal surgery encompasses various delicate procedures involving internal portions of the eye, such as the vitreous humor and the retina. Different vitreoretinal surgical procedures are used, sometimes with lasers, to improve visual sensory performance in the treatment of many eye diseases, including epimacular membranes, diabetic retinopathy, vitreous hemorrhage, macular hole, detached retina, and complications of cataract surgery, among others.

During vitreoretinal surgery, an ophthalmologist typically uses a surgical microscope to view the fundus through the cornea, while surgical instruments that penetrate the sclera may be introduced to perform any of a variety of different procedures. The surgical microscope provides imaging and optionally illumination of the fundus during vitreoretinal surgery. The patient typically lies supine under the surgical microscope during vitreoretinal surgery and a speculum is used to keep the eye exposed. Depending on a type of optical system used, the ophthalmologist has a given field of view of the fundus, which may vary from a narrow field of view to a wide field of view that can extend to peripheral regions of the fundus.

Modern ophthalmic surgery, such as vitreoretinal surgery, is typically performed with complex equipment, such as specialized surgical probes, infusion pumps, pneumatic valves, pneumatic pumps, pneumatic compressors, aspirators, illumination sources, cooling fans, and lasers, among others. At least a portion of the surgical equipment for ophthalmic surgery may be integrated into an ophthalmic surgical system, such as the CONSTELLATION® Vision System. The various surgical and related equipment associated with the ophthalmic surgical system may generate significant sound during use, which may be perceived by surgical personnel as unwanted acoustical noise that is unpleasant and adversely affects working conditions in the operating room.

SUMMARY

The disclosed embodiments of the present disclosure provide active noise cancellation in ophthalmic surgical systems. The methods and systems for active noise cancellation in ophthalmic surgical systems disclosed herein may include an active noise cancellation in ophthalmic surgical system chassis, in a surgical air compressor, and in a reciprocating surgical probe.

In one aspect, a disclosed ophthalmic surgical system includes a pneumatic actuator, an infusion system, a cooling fan, and an active noise cancellation system. In the ophthalmic surgical system, the active noise cancellation system may further include a first microphone, a speaker, and a digital signal processor (DSP). The DSP may have access to memory media storing instructions executable by the DSP to detect a noise waveform captured by the first microphone, the noise waveform resulting from operation of at least one of the pneumatic actuator, the infusion system, and the cooling fan. In the ophthalmic surgical system, the instructions may further be executable by the DSP to generate a noise cancellation waveform to cancel the noise waveform, and cause the noise cancellation waveform to be output to the speaker.

In any of the disclosed embodiments of the ophthalmic surgical system, the pneumatic actuator may include a dual-channel actuator enabled to drive a reciprocating surgical probe.

In any of the disclosed embodiments of the ophthalmic surgical system, the active noise cancellation system may further include a second microphone, while the instructions may further be executable by the DSP to detect a feedback waveform captured by the second microphone, the feedback waveform indicative of a total noise generated by the ophthalmic surgical system, the total noise including the noise waveform and the noise cancellation waveform, and generate the noise cancellation waveform based at least in part on the feedback waveform.

In any of the disclosed embodiments, the ophthalmic surgical system may further include an audio power amplifier for amplifying the noise cancellation waveform output to the speaker.

In another aspect, a surgical air compressor is disclosed for use in an operating room. The surgical air compressor may include an active noise cancellation system. In the surgical air compressor, the active noise cancellation system may further include a first microphone, a speaker, and a DSP. In the surgical air compressor, the DSP may have access to memory media storing instructions executable to detect a noise waveform captured by the first microphone, the noise waveform resulting from operation of the surgical air compressor to compress air, generate a noise cancellation waveform to cancel the noise waveform, and cause the noise cancellation waveform to be output to the speaker.

In any of the disclosed embodiments of the surgical air compressor, the surgical air compressor may provide compressed air to an ophthalmic surgical system further including a pneumatic actuator, an infusion system, and a cooling fan.

In any of the disclosed embodiments of the surgical air compressor, the active noise cancellation system may include a second microphone, while the instructions may further be executable by the DSP to detect a feedback waveform captured by the second microphone, the feedback waveform indicative of a total noise generated by the surgical air compressor, the total noise including the noise waveform and the noise cancellation waveform, and generate the noise cancellation waveform based at least in part on the feedback waveform.

In any of the disclosed embodiments, the surgical air compressor may further include an audio power amplifier for amplifying the noise cancellation waveform output to the speaker.

In yet a further aspect, a reciprocating surgical probe is disclosed for use in ophthalmic surgery. The reciprocating surgical probe may include an active noise cancellation system. In the reciprocating surgical probe, the active noise cancellation system may include two pressure sensors, a speaker, and a logic controller. In the reciprocating surgical probe, the logic controller may have access to memory media and may be enabled to detect actuation of the reciprocating surgical probe from a signal generated by at least one of the pressure sensors. In the reciprocating surgical probe, the signal may be indicative of a noise waveform generated by the reciprocating surgical probe during operation. In the reciprocating surgical probe, the logic controller may be further enabled to retrieve, from the memory media, a noise cancellation waveform corresponding to the noise waveform, and cause the noise cancellation waveform to be output to the speaker.

In any of the disclosed embodiments of the reciprocating surgical probe, the reciprocating surgical probe may be actuated by compressed air from an ophthalmic surgical system further including a pneumatic actuator, an infusion system, and a cooling fan.

In any of the disclosed embodiments of the reciprocating surgical probe, the pneumatic actuator may be a dual-channel actuator enabled to drive the reciprocating surgical probe. In the reciprocating surgical probe, each of the two pressure sensors may be respectively coupled to a channel of the dual-channel actuator.

In any of the disclosed embodiments, the reciprocating surgical probe may further include a power source to power the active noise cancellation system.

In any of the disclosed embodiments of the reciprocating surgical probe, the reciprocating surgical probe including the active noise cancellation system may be a handheld surgical probe. In any of the disclosed embodiments, the reciprocating surgical probe may be a vitrectomy probe.

In any of the disclosed embodiments of the reciprocating surgical probe, the noise waveform may be prerecorded and stored on the memory media.

In any of the disclosed embodiments of the reciprocating surgical probe, the noise waveform may be selected from a plurality of noise waveforms stored on the memory media based on a duty-cycle setting of the reciprocating surgical probe.

In any of the disclosed embodiments of the reciprocating surgical probe, the reciprocating surgical probe may operate at a rate of up to 1,000 cutting cycles per second.

In any of the disclosed embodiments of the reciprocating surgical probe, the speaker may include a piezoelectric actuator.

BRIEF DESCRIPTION OF THE DRAWINGS

For a more complete understanding of the present invention and its features and advantages, reference is now made to the following description, taken in conjunction with the accompanying drawings, in which.

DESCRIPTION OF PARTICULAR EMBODIMENT(S)

Figure 1:
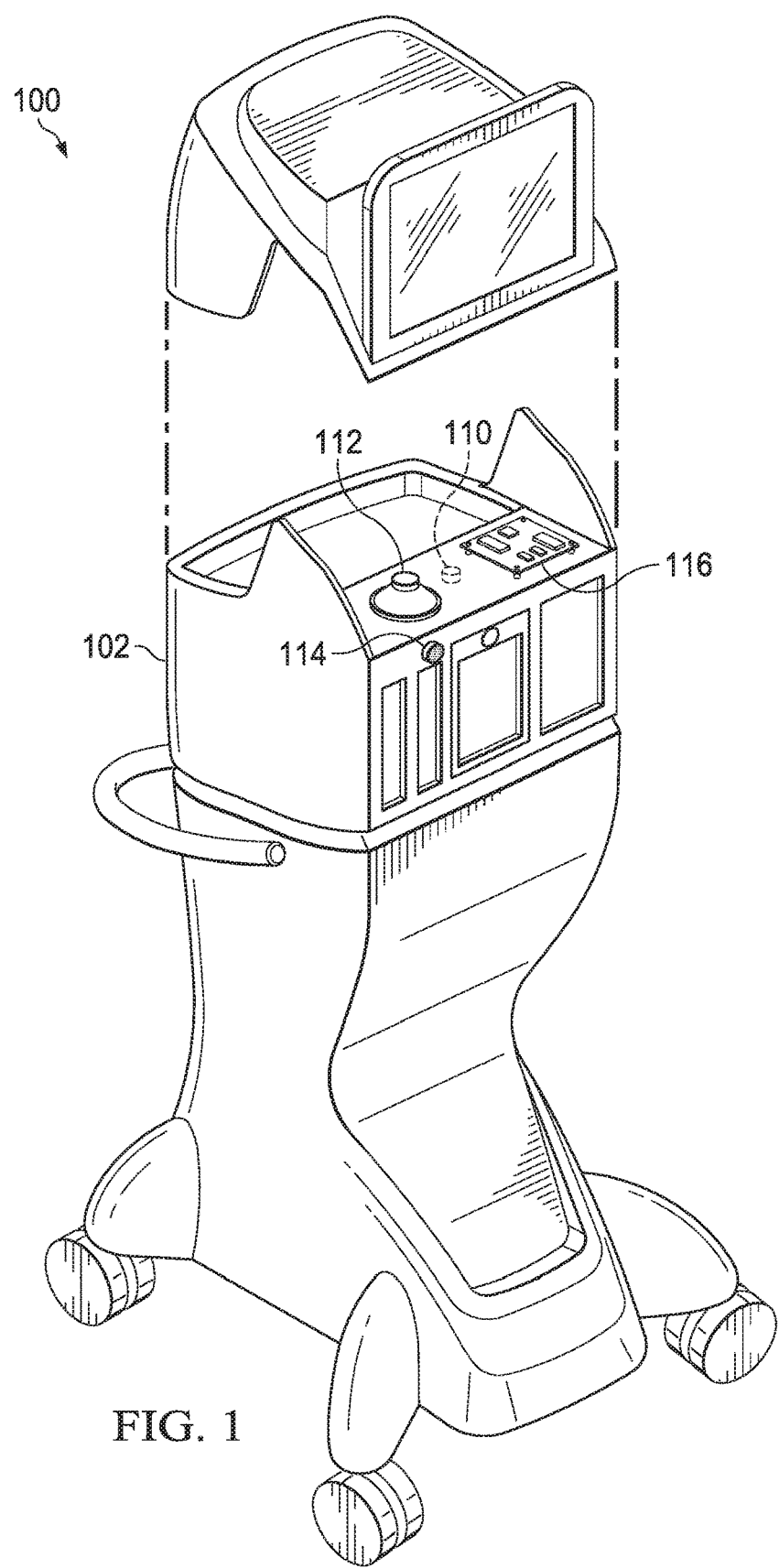
FIG. 1 is a depiction of an embodiment of a surgical noise cancellation system.

In the following description, details are set forth by way of example to facilitate discussion of the disclosed subject matter. It should be apparent to a person of ordinary skill in the field, however, that the disclosed embodiments are exemplary and not exhaustive of all possible embodiments.

As noted above, surgical equipment associated with the ophthalmic surgery may generate significant noise in the operating room, which may be adversely affect working conditions in the operating room. The noise from the surgical equipment may cause surgical personnel to become fatigued and may hinder proper communication during surgery. Furthermore, excessive noise generated by certain components in an ophthalmic surgical system may constrain operational design and function of surgical equipment. For example, the amount of cooling that a cooling fan can provide may be limited by a noise level generated by the cooling fan, which may, in turn, constrain the amount of heat generated by the ophthalmic surgical system that may be related to an operational parameter, such as frequency or pressure, as examples.

As will be described in further detail, the inventors of the present disclosure have developed active noise cancellation in ophthalmic surgical systems. The methods and systems for active noise cancellation in ophthalmic surgical systems disclosed herein may include an active noise cancellation in ophthalmic surgical system chassis, in a surgical air compressor, and in a reciprocating surgical probe. The methods and systems for active noise cancellation in ophthalmic surgical systems disclosed herein may reduce ambient noise levels and may result in a quieter operating room, which is desirable for surgical personnel. The methods and systems for active noise cancellation in ophthalmic surgical systems disclosed herein may enable expanded operational parameters of surgical equipment, by increasing an operational range at which certain elements may be used. For example, using active noise cancellation in ophthalmic surgical systems, as disclosed herein, a given cooling fan may be operated at higher fan speeds (and higher cooling rates) when not constrained by acoustical noise generated by the cooling fan, thereby enabling higher thermal loads to be generated in the surgical equipment cooled by the cooling fan. The methods and systems for active noise cancellation in ophthalmic surgical systems disclosed herein may further enable the use of different technologies that would otherwise not be suitable due to excessive noise, such as certain aspirators, air compressors, pneumatic valves, among others. The methods and systems for active noise cancellation in ophthalmic surgical systems disclosed herein may reduce the noise generated by hand-held surgical probes, such as vitrectomy probes that reciprocate at high frequencies up to about 1,000 cutting cycles per second. The methods and systems for active noise cancellation in ophthalmic surgical systems disclosed herein may further be used without the addition of sound baffling or a reduction in cooling air flow to the ophthalmic surgical system.

Referring now to the drawings, FIG. 1, illustrates selected elements of an embodiment of a surgical noise cancellation system 100. In FIG. 1, surgical noise cancellation system includes a chassis 102, which is shown as a component of an ophthalmic surgical system 104. In one embodiment, ophthalmic surgical system 104 is the CONSTELLATION® Vision System, though other ophthalmic surgical systems may include chassis 102. Thus, chassis 102 of ophthalmic surgical system 104 may include infusion pumps, pneumatic valves, pneumatic pumps, pneumatic compressors, aspirators, illumination sources, cooling fans, and lasers, among others, which are not shown for descriptive clarity.

In FIG. 1, the equipment included in ophthalmic surgical system 104, and in particular in chassis 102, may generate significant amounts of acoustical noise when operated. For example, ophthalmic surgical system 104 may be supplied with compressed air to enable pneumatic operation of various devices, such as a hand-held surgical probe that is powered and controlled from chassis 102. Accordingly, chassis 102 may include various components for pneumatic actuation and control that result in acoustical noise being generated. In a further example, the equipment housed within chassis 102 may be cooled using cooling fans included in chassis 102. During operation, the cooling fans may generate a certain level of acoustical noise that may depend upon a fan speed of the cooling fans, such that higher fan speeds result in more acoustical noise being created. As a result of the foregoing, ophthalmic surgical system 104 may generate different types of acoustical noise, including steady state, intermittent, periodic, and event-driven types of acoustical noise. Steady state acoustical noise may result from a constant noise source, such as from a cooling fan. Intermittent, periodic, impulse, event-driven, and other types of varying acoustical noise may result from certain kinds of equipment, such as infusion pumps, solenoid-operated pneumatic valves, pneumatic pumps, air cylinders, motors driving peristaltic pumps, and venturi aspirators, as non-limiting examples.

As shown in FIG. 1, ophthalmic surgical system 104 may include active noise cancellation components to mitigate the acoustical noise and lower the overall noise levels generated by ophthalmic surgical system 104 in operation. Specifically, chassis 102 may include a noise microphone 110, a feedback microphone 114, a speaker 112, and an electronic device 116. Noise microphone 110 may be any of a variety of different types of microphones that convert a pressure waveform into an electrical signal and may be placed at a location within chassis 102 to capture a noise waveform indicative of the acoustical noise generated by various sources, as described above. The location at which noise microphone 110 is placed within chassis 102 may vary in different embodiments. In some embodiments, noise microphone 110 is placed in proximity to the sources of noise in chassis 102, as described above. Feedback microphone 114 may be any of a variety of different types of microphones that convert a pressure waveform into an electrical signal and may be placed at a location within or near chassis 102 to capture a feedback waveform indicative of the overall acoustical output generated by ophthalmic surgical system 104, including the noise waveform and a noise cancellation waveform generated by speaker 112 that coverts an electrical signal into a pressure waveform (an acoustical signal). It is noted that in particular embodiments, speaker 112 may be implemented using a portion of chassis 102, such as a panel or panel element, that is driven by speaker 112 to generate the acoustical signal representing the feedback waveform.

As shown in FIG. 1, electronic device 116 may acquire (or sample) the noise waveform, the feedback waveform, or both, and may generate the noise cancellation waveform that is output to speaker 112, which physically cancels the unwanted noise generated by ophthalmic surgical system 104. In various embodiments, the noise cancellation waveform may include an inverse waveform of the noise waveform. Electronic device 116 may accordingly include components for signal conditioning (such as signal amplifiers and filters), signal acquisition (such as analog-to-digital converters (ADCs)), digital signal processing (DSP) or more general processing, storage of signals (such as memory media), signal generation (such as digital-to-analog converters (DACs)), and other related functionality. In particular, the DSP (or other processor) may perform various signal processing operations that may be customized using code or instructions executed by the DSP. For example, the DSP included in electronic device 116 may perform feedback control, among various different types of control algorithms (see also FIG. 2).

It is noted that electronic device 116, among other components described herein, may operate using a power source in chassis 102. In some embodiments, electronic device 116 may be operated using a battery. It is further noted that the connections between electronic device 116 and the other components described herein may be wired or wireless connections in different embodiments.

In addition to the embodiment of the surgical noise cancellation system depicted in FIG. 1, additional embodiments of active noise cancellation in an ophthalmic surgical system may be implemented, as described below in the example implementations shown in FIG. 3 (a surgical compressor with active noise cancellation 300) and FIG. 4 (a reciprocating surgical probe with active noise cancellation 400).

Figure 2:
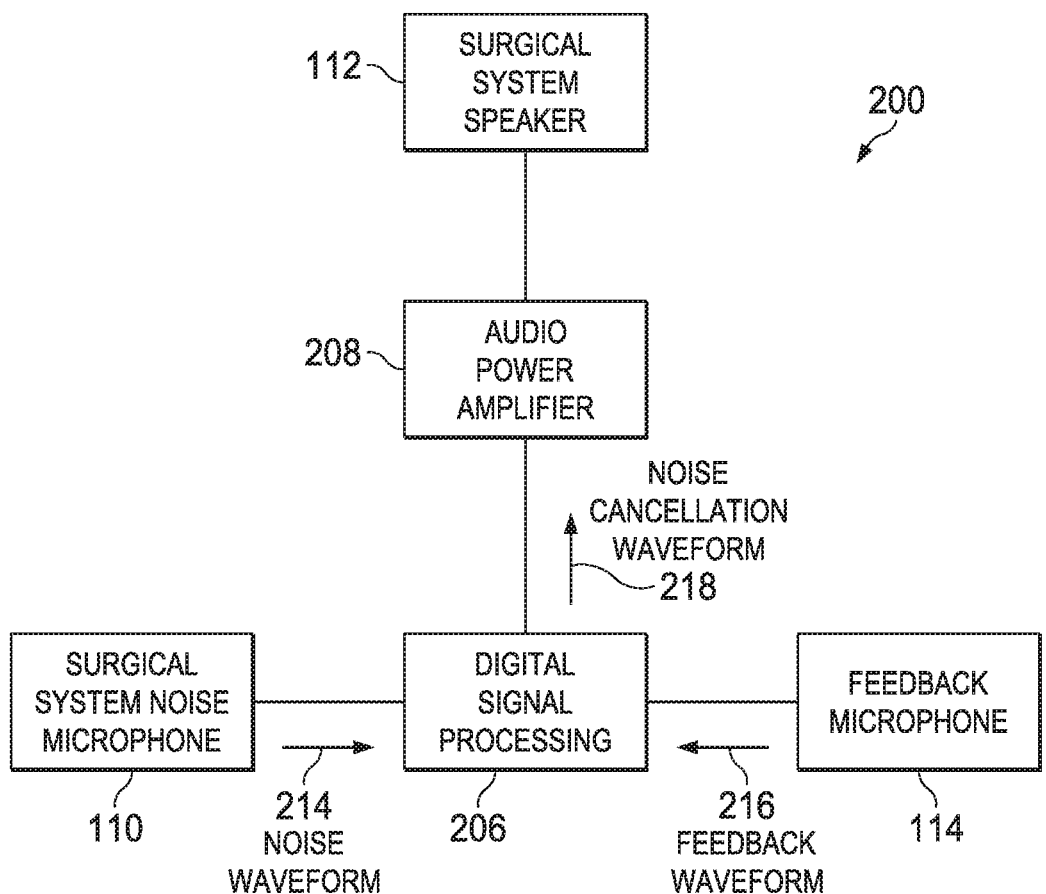
FIG. 2 is a diagram of selected embodiments of a surgical noise cancellation system.

Referring now to FIG. 2, selected elements of an embodiment of a surgical noise cancellation system 200 are shown. In FIG. 2, surgical noise cancellation system 200 is shown as a modular, schematic block diagram that may represent component and functionality of active noise cancellation in the ophthalmic surgical systems disclosed herein, such as ophthalmic surgical system 100 (see FIG. 1), surgical compressor with active noise cancellation 300 (see FIG. 3), and reciprocating surgical probe with active noise cancellation 400 (see FIG. 4). It is further noted that certain circuit elements for signal operations (such as amplifiers, filters, ADCs, DACs) have been omitted in FIG. 2 for descriptive clarity to better explain the active noise cancellation functionality contemplated herein.

In FIG. 2, noise microphone 110 may generate noise waveform 214 from a source of acoustical noise, as described above. Accordingly, noise microphone 110 may be located in proximity to the physical source of the acoustical noise being actively cancelled, or at a location to selectively capture the acoustical noise source. Noise waveform 214 may be received by a digital signal processing (DSP) 206 in digital form as signal data indicative of the acoustical noise source.

In FIG. 2, the sampling of noise waveform 214 in surgical noise cancellation system 200 may occur according to different methods and active noise cancellation processes. In a first example, noise waveform 214 may be observed to be relatively constant, such as when discrete noise events occur that are substantially the same noise event, whether at regular or irregular intervals. In such a case of a relatively constant waveform for noise waveform 214 in the first example, noise waveform 214 may be sampled using noise microphone 110 relatively infrequently, for example, as a reference signal that is stored once and repeatedly retrieved (such as from a memory media). In a second example, noise waveform 214 may exhibit ongoing variation, for example, when corresponding surgical equipment is in constant use under varying conditions or settings. In such a case of a varying waveform for noise waveform 214 in the second example, noise waveform 214 may be sampled using noise microphone 110 relatively frequently, for example, in a constant fashion, such as using a buffered signal acquisition to continuously sample noise waveform 214. In still other examples, different methods for sampling noise waveform 214 may be used. In a third example where the acoustical noise source is constant and occurs repetitively, noise microphone 110 may be a simple pressure transducer that merely detects the presence or absence of acoustical noise, such that noise waveform 214 is not used (not shown in FIG. 2). In the third example, noise cancellation waveform 218 may be generated once and stored in a memory media accessible to a controller (not shown). In the third example, noise microphone 110 generates a trigger signal that is used by the controller to output noise cancellation waveform 218. It is noted that the third example may operate without DSP 206 or another processor by using a relatively simple logic controller, which may be very small and may consume very low amounts of electrical power.

In some embodiments of surgical noise cancellation system 200 shown in FIG. 2, DSP 206 may receive noise waveform 214 and may generate noise cancellation waveform 218 in response. DSP 206 may use any suitable algorithm for generating noise cancellation waveform 218 that results in active cancellation of noise waveform 214. Noise cancellation waveform 218 may be received by audio power amplifier 208, which may be regulated or controlled by DSP 206, to amplify and prepare noise cancellation waveform 218 for output by speaker 112. After noise cancellation waveform 218 is output by speaker 112, the acoustical noise source may be cancelled such that noise waveform 214 is no longer perceptible or is largely eliminated from being perceptible, even though noise waveform 214 continues to be generated by the acoustical noise source.

Also shown in surgical noise cancellation system 200 in FIG. 2 is feedback microphone 114, which may be optional in particular embodiments. Feedback microphone 114 may be placed at a location within or near surgical noise cancellation system 200 to capture feedback waveform 218. Feedback waveform 218 may be indicative of a cumulative acoustical output of surgical noise cancellation system 200, including the noise waveform 214 and noise cancellation 218. In other words, feedback waveform 216 may represent the overall output acoustical noise level generated by surgical noise cancellation system 200 using active noise cancellation. Feedback waveform 216 may be received by DSP 206 and may be incorporated into a suitable algorithm for generating noise cancellation waveform 218. For example, depending on an amplitude of feedback waveform 216, DSP 206 may modulate an amplitude of noise cancellation waveform 218 to minimize feedback waveform 216. The use of feedback waveform 216 may be referred to as feedback regulation (or control) in surgical noise cancellation system 200. It is noted that various combinations of feedback control may be implemented using surgical noise cancellation system 200.

Figure 3:
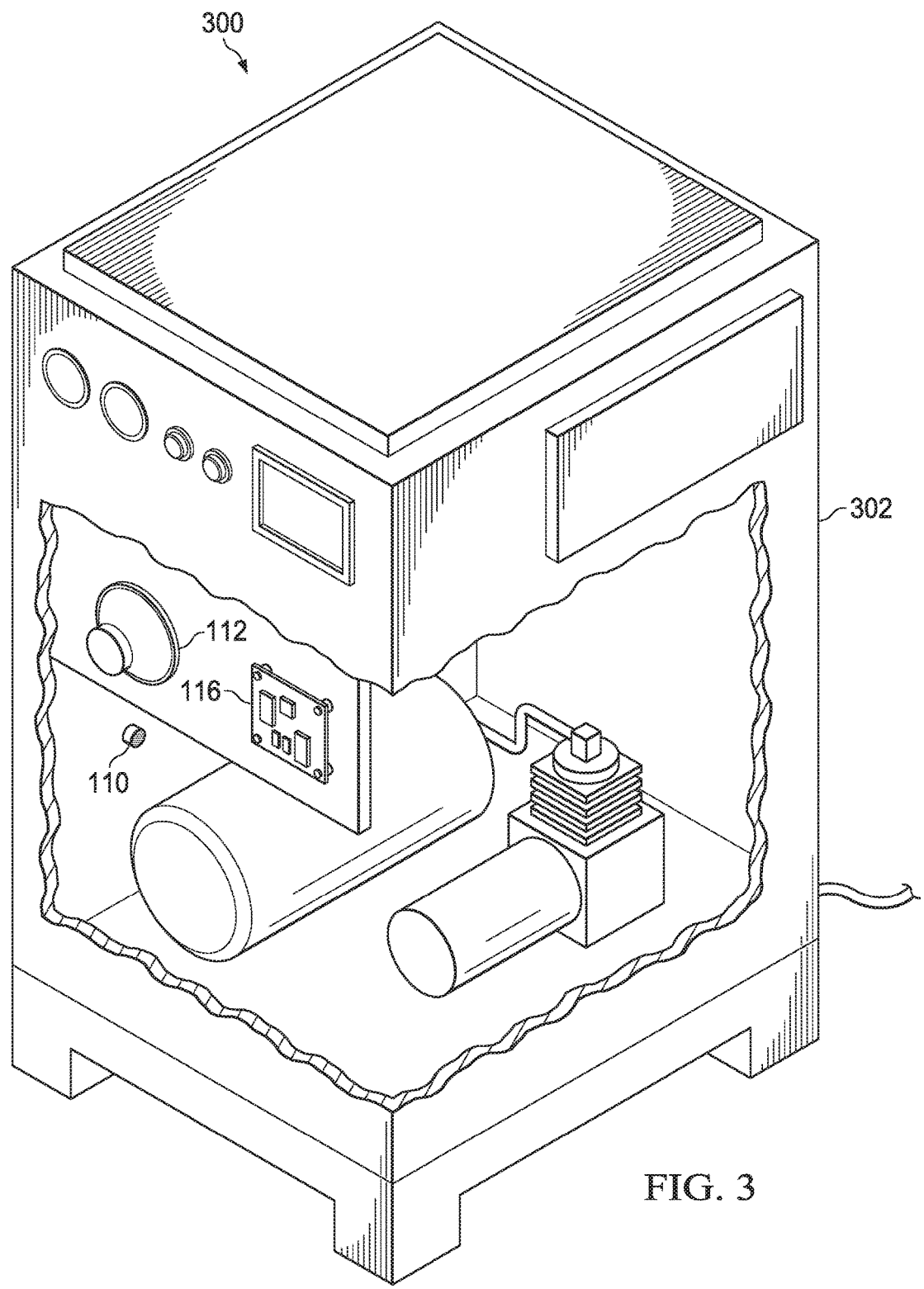
FIG. 3 is a depiction of an embodiment of a surgical compressor with active noise cancellation.

Referring now to FIG. 3, selected elements of an embodiment of surgical compressor with active noise cancellation 300 are shown. In FIG. 3, surgical compressor 302 may be an air compressor for use in an operating room during surgery having active noise cancellation integrated therein. Typically, ophthalmic surgical systems, among other types of surgical equipment, used during surgery are supplied with compressed air provided by a central facility, such as a hospital physical plant and delivered via line feed. Alternatively, when no central source of compressed air is available, compressed air tanks may be used, but at a significant cost and with logistical constraints, such as to order and supply the air tanks and to monitor and exchange the air tanks. The use of an air compressor in such surgical environments is generally not possible due to the high level of acoustical noise generated by air compressor motors during operation.

As shown in FIG. 3, surgical compressor with active noise cancellation 300 provides low cost compressed air for surgical applications at low cost and with minimal logistical constraints, while eliminating the undesired acoustical noise. Specifically, surgical compressor with active noise cancellation 300 may be equipped with noise microphone 110, speaker 112, and electronic device 116 to enable active noise cancellation, as described herein. It is noted that the noise waveform generated by surgical compressor with active noise cancellation 300 may be relatively constant and may repeat irregularly, such that the active noise cancellation used may be designed accordingly. In various example implementations, surgical compressor with active noise cancellation 300 may operate according to the first example or the third example described above with respect to FIG. 2.

Figure 4:
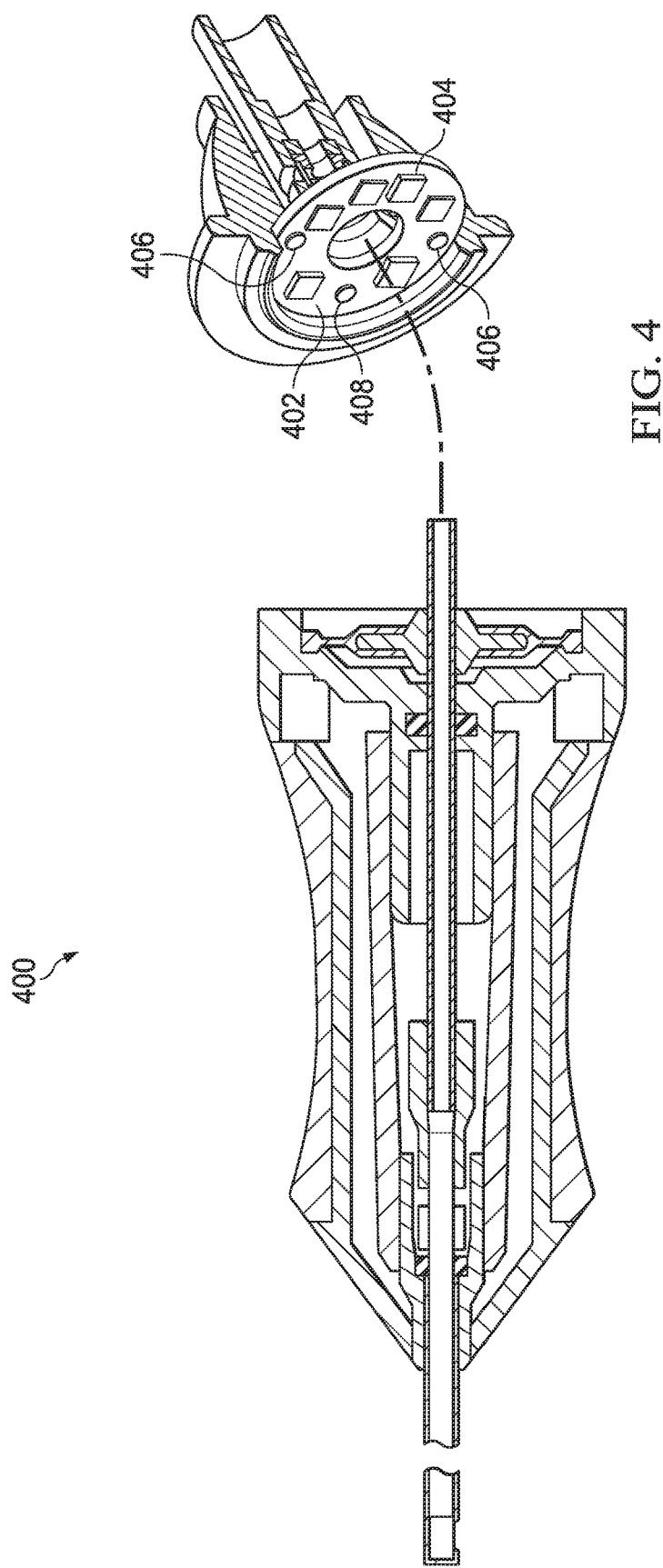
FIG. 4 is a depiction of an embodiment of a reciprocating surgical probe with active noise cancellation.

Referring now to FIG. 4, selected elements of an embodiment of a reciprocating surgical probe with active noise cancellation 400 are shown. In FIG. 4, reciprocating surgical probe with active noise cancellation 400 may include functionality of a surgical probe, such as an ULTRAVIT® surgical probe, which is a reciprocating surgical probe using dual pneumatic actuation inputs that enable control of the duty-cycle of the reciprocating cutter. In various embodiments, reciprocating surgical probe with active noise cancellation 400 is a hand-held or finger-held instrument that is used by a surgeon during ophthalmic surgery for various operations, such as vitrectomy. Because surgical probes may include a mechanism that may reciprocate at very high cutting rates, such as up to 1,000 cutting cycles per second or higher, significant acoustical noise may be generated during operation of surgical probes, which is undesirable in the surgical environment of the operating room.

As shown in FIG. 4, reciprocating surgical probe with active noise cancellation 400 includes electronic device 402, which may be similar to electronic device 116 (see FIG. 1). Specifically, electronic device 402 may include two pressure sensors 406, a logic controller 404, and a speaker 408. Furthermore, electronic device 402 may include a battery to power the components included therein, which has been omitted for descriptive clarity. Logic controller 404 may include or may have access to memory media included with electronic device 402. In various embodiments, electronic device 402 may include a printed-circuit board (PCB), and may accordingly be miniaturized to fit in a form-factor that is suitable for inclusion with a surgical probe. As shown in FIG. 4, electronic device 402 may take the form of a circular PCB having a central opening that mates within the construction of a reciprocating surgical probe for hand-held or finger-held operation by a surgeon.

By placing speaker 408 within reciprocating surgical probe 400, the source of the noise waveform (moving parts of probe 400) and the source of the noise cancellation waveform are effectively co-located, which may enable an omnidirectional noise cancelling effect. In various embodiments, speaker 408 may be driven with a comparable level of audio power in the noise cancellation waveform as detected in the noise waveform.

In operation, reciprocating surgical probe 400 may operate according to the second example described above with respect to FIG. 2. Specifically, each pressure sensor 406 may be enabled to trigger on a vibration or pressure wave resulting from the oscillation when the reciprocating surgical probe 400 is activated in each direction, respectively. The trigger from pressure sensor 406 is received by logic controller 404, which may then cause a predetermined noise cancellation waveform to be retrieved and output to speaker 408, which may be a miniature piezoelectric acoustic transducer. The functionality may be similar to playing an audio file by an electronic device. The noise cancellation waveform is played by speaker 408 with each instance of manual actuation of probe 400 and is a discrete sound event, rather than a continuous noise cancellation sound. In this manner, the overall noise level during operation of reciprocating surgical probe 400 may be significantly reduced, which is desirable.

The noise cancellation waveform to be played by speaker 408 may be a pre-determined sound (for example, a sound file stored in microprocessor memory). The use of a predetermined sound for the noise cancellation waveform is expected to be effective, because the motion of the cutter closing and opening within probe 400 is a consistent action that generally produces a predictable sound. In some embodiments, two different sound files are stored and are used for the noise cancellation waveform: a first sound file may be used for the opening action of the cutter and a second sound file may be used for the closing action of the cutter. In particular embodiments, either the first sound file or the second sound file may be played as the noise cancellation waveform based on triggering from each of pressure sensors 406, respectively, which may be located in proximity to each of the two pneumatic lines that drive the reciprocating action of probe 400. It is noted that the two pneumatic lines may be driven by a corresponding dual-channel pneumatic actuator, which may be configurable by the user. In various implementations, the use of a simple pressure sensor that is responsive to a pressure pulse in a binary manner (pressure/no pressure) may be suitable for triggering the respective noise cancellation waveform. In this manner, pressure sensors 406 may have very short response times relative to the duration of a cutting half-cycle of probe 400, such that electronic device 402 may respond by outputting the noise cancellation wave at an appropriate time.

In some embodiments, more than one kind of the noise cancellation waveform (or pairs of noise cancellation waveforms, for opening and closing of the cutter) may be stored and accessed. For example, pressure sensors 406 may be enabled to detect a duty cycle of reciprocating surgical probe with active noise cancellation 400 and may retrieve a particular noise cancellation waveform that corresponds to the duty cycle. Other operational parameters may also be indexed to different specific copies of the noise cancellation waveform, such as frequency, aspiration flow rate or pressure, pneumatic pressure, etc.

As described above using pressure sensors 406, reciprocating surgical probe 400 may employ a self-contained noise cancellation scheme that may operate without external signals or synchronization. In other embodiments, reciprocating surgical probe 400 may receive control signals or power from a surgical console, such as included in chassis 102. When a control signal from the surgical console is used, an additional electrical connection (not shown) may be included in reciprocating surgical probe 400 to receive timing control signals for generating the noise cancellation waveforms, rather than from triggering using pressure sensors 406, as described above.

In yet other embodiments, speaker 408 may output a continuous noise cancellation sound while reciprocating surgical probe 400 is operated, rather than distinct instances of a noise cancellation waveform each time that the cutter is actuated. In this case, different sound files may be used for different cut rates and duty cycles, among other parameters. In still other embodiments, reciprocating surgical probe 400 may include a microphone (instead or in addition to pressure sensors 406) to adapt to the actual noise waveform produced in real time, for example, as described above with respect to FIGS. 1 and 2.

As disclosed herein, active noise cancellation is employed to address unwanted acoustical noise generated by various equipment associated with an ophthalmic surgical system. Active noise cancellation may be used within a chassis of the ophthalmic surgical system, within an air compressor used with the ophthalmic surgical system, and within a reciprocating surgical probe used with the ophthalmic surgical system.

The above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

What is claimed is:

1. A reciprocating surgical probe for use in ophthalmic surgery, comprising:
   an active noise cancellation system further comprising:
      two pressure sensors;
      a speaker; and
      a logic controller having access to memory media and enabled to:
   detect actuation of the reciprocating surgical probe from a signal generated by at least one of the two pressure sensors, wherein the signal is indicative of a noise waveform generated by the reciprocating surgical probe during operation;
   retrieve, from the memory media, a noise cancellation waveform corresponding to the noise waveform; and
   cause the noise cancellation waveform to be output to the speaker.

2. The reciprocating surgical probe of claim 1, wherein the reciprocating surgical probe is actuated by compressed air from an ophthalmic surgical system further comprising:
   a pneumatic actuator;
   an infusion system; and
   a cooling fan.

3. The reciprocating surgical probe of claim 2, wherein the pneumatic actuator is a dual-channel actuator enabled to drive the reciprocating surgical probe, and wherein each of the two pressure sensors is respectively coupled to a channel of the dual-channel actuator.

4. The reciprocating surgical probe of claim 1, further comprising:
   a power source to power the active noise cancellation system.

5. The reciprocating surgical probe of claim 1, wherein the reciprocating surgical probe including the active noise cancellation system is a handheld surgical probe.

6. The reciprocating surgical probe of claim 5, wherein the reciprocating surgical probe is a vitrectomy probe.

7. The reciprocating surgical probe of claim 1, wherein the noise waveform is prerecorded and stored on the memory media.

8. The reciprocating surgical probe of claim 1, wherein the noise waveform is selected from a plurality of noise waveforms stored on the memory media based on a duty-cycle setting of the reciprocating surgical probe.

9. The reciprocating surgical probe of claim 1, wherein the reciprocating surgical probe operates at a rate of up to 1,000 cutting cycles per second.

10. The reciprocating surgical probe of claim 1, wherein the speaker includes a piezoelectric actuator.

* * * * *